(12) United States Patent
Zan et al.

(10) Patent No.: US 11,635,400 B2
(45) Date of Patent: Apr. 25, 2023

(54) GAS SENSOR

(71) Applicant: NATIONAL CHIAO TUNG UNIVERSITY, Hsinchu (TW)

(72) Inventors: Hsiao-Wen Zan, Hsinchu (TW); Hsin-Fei Meng, Hsinchu (TW); Chien-Lung Wang, Hsinchu (TW); Sheng-Fu Horng, Hsinchu (TW); Hsuan Chu, Hsinchu (TW); Wei-Lun Chen, Hsinchu (TW); Ting-Hsuan Huang, Hsinchu (TW); Pin-Hsuan Li, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 59 days.

(21) Appl. No.: 16/997,103

(22) Filed: Aug. 19, 2020

(65) Prior Publication Data
US 2021/0255130 A1 Aug. 19, 2021

(30) Foreign Application Priority Data

Feb. 14, 2020 (TW) .................................. 109104649

(51) Int. Cl.
*G01N 27/12* (2006.01)
*G01N 27/04* (2006.01)

(52) U.S. Cl.
CPC .......... *G01N 27/125* (2013.01); *G01N 27/04* (2013.01); *G01N 27/041* (2013.01); *G01N 27/121* (2013.01)

(58) Field of Classification Search
CPC .... G01N 27/125; G01N 27/04; G01N 27/041; G01N 27/121
See application file for complete search history.

(56) References Cited

U.S. PATENT DOCUMENTS

| | | | | | |
|---|---|---|---|---|---|
| 3,983,527 | A | * | 9/1976 | Ohsato | ...................... B60S 1/00 338/35 |
| 4,635,027 | A | * | 1/1987 | Miyoshi | ............... G01N 27/126 338/34 |

FOREIGN PATENT DOCUMENTS

| | | | | |
|---|---|---|---|---|
| TW | I615611 | * | 2/2018 | ........... G01N 27/127 |
| TW | I615611 | B | 2/2018 | |

OTHER PUBLICATIONS

Jin Wu et al., "Extremely Deformable, Transparent, and High-Performance Gas Sensor Based on Ionic Conductive Hydrogel", ACS Applied Materials & Interfaces, 11, pp. 2364-2373 (2019).
Myungwoo Son et al., "Charge transfer in graphene/polymer interfaces for CO2 detection", Nano Research, 11(7), pp. 3529-3536 (2018).

* cited by examiner

*Primary Examiner* — Benjamin R Schmitt
(74) *Attorney, Agent, or Firm* — Lando & Anastasi, LLP

(57) ABSTRACT

A gas sensor for sensing a gas in a humid environment includes a first electrode layer, a second electrode layer that is spaced apart from the first electrode layer, and a gas sensing layer that electrically interconnects the first electrode layer and the second electrode layer. The gas sensing layer is made of a hygroscopic electrically insulating material.

14 Claims, 5 Drawing Sheets

GAS SENSOR

CROSS-REFERENCE TO RELATED APPLICATION

This application claims priority of Taiwanese Patent Application No. 109104649, filed on Feb. 14, 2020.

FIELD

The present disclosure relates to a sensor, and more particularly to a gas sensor.

BACKGROUND

Taiwanese Invention Patent No. I615611 discloses a gas detector including an electrode unit that is adapted to be electrically connected to an electrical detector, and a sensing unit. The electrode unit includes a first electrode layer and a second electrode layer that is spaced apart from the first electrode layer. The second electrode layer has two electrode surfaces opposite to each other, and is formed with a plurality of through holes each extending through the electrode surfaces. The sensing unit includes a sensing layer for detecting a gas, which is connected to the first electrode layer and the second electrode layer. The sensing layer is made of a material containing one of the following functional groups: a fluorenyl-based functional group, a triphenylamine-based and fluorenyl-based functional group, a phenylene vinylene-based functional group, and a dithiophenebenzodithiophenyl-based and thioenothiophenyl-based functional group, such as poly[(9,9-dioctylfluorene-co-benzothiadiazole), poly[(4,8-bis[5-(2-ethylhexyl) thiophene-2-yl]benzo[1,2-b:4,5-b']dithiophene)-2,6-diyl-alt-(4-(2-ethylhexanoyl)-thieno[3,4-b]thiophene))-2,6-diyl] (synonyms: poly[[4,8-bis[5-(2-ethylhexyl)-2-thienyl]benzo [1,2-b:4,5-b']dithiophene-2,6-diyl][2-(2-ethyl-1-oxohexyl) thieno[3,4-b]thiophenediyl]]; PBDTTT-C-T), poly{4,8-bis (5-(2-ethylhexyl)thiophen-2-yl)benzo[1,2-b:4,5-b'] dithiophene-2,6-diyl-4-(2-ethylhexyloxycarbonyl)-3-fluoro-thieno[3,4-b]thiophene-2,6-diyl}, etc.

The gas detector disclosed in the aforesaid patent is capable of detecting amines (e.g., ammonia), aldehydes, ketones, nitric oxide, ethanol, nitrogen dioxide, carbon dioxide, ozone, a sulfide gas and other types of gases. However, the material for making the sensing layer is relatively expensive, and thus, the manufacturing cost of the gas detector is high.

SUMMARY

Therefore, an object of the present disclosure is to provide a gas sensor that can alleviate at least one of the drawbacks of the prior art.

According to the present disclosure, the gas sensor includes a first electrode layer, a second electrode layer that is spaced apart from the first electrode layer, and a gas sensing layer that electrically interconnects the first electrode layer and the second electrode layer. The gas sensing layer is made of a hygroscopic electrically insulating material.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
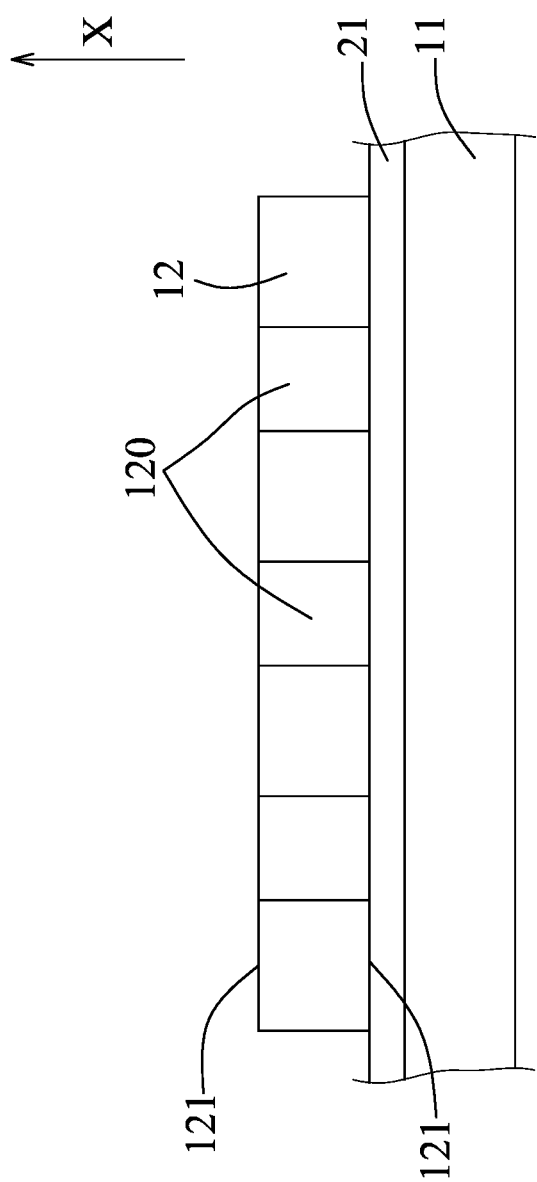
FIG. 1 is a fragmentary schematic sectional view illustrating a first embodiment of a gas sensor according to the present disclosure.

Before the present disclosure is described in greater detail, it should be noted that where considered appropriate, reference numerals or terminal portions of reference numerals have been repeated among the figures to indicate corresponding or analogous elements, which may optionally have similar characteristics.

Referring to FIG. 1, a first embodiment of the gas sensor according to the present disclosure is configured to be electrically connected to an electrical detector (not shown in the figure) for sensing a gas in a humid environment. The electrical detector is capable of detecting electrical change when the gas sensor is in contact with a gas to be detected, such as ammonia ($NH_3$), acetone, nitric oxide (NO), carbon monoxide (CO), hydrogen sulfide ($H_2S$), etc. The electrical change may include resistance change and/or current change. In an exemplary embodiment, the electrical change to be detected by the electrical detector is current change.

According to the present disclosure, the gas sensor includes a first electrode layer 11, a second electrode layer 12 that is spaced apart from the first electrode layer 11, and a gas sensing layer 21.

The first electrode layer 11 may have a length ranging from 1 mm to 10 mm, a width ranging from 1 mm to 10 mm, and a thickness ranging from 250 nm to 400 nm.

The second electrode layer 12 has two electrode surfaces 121 opposite to each other, and is formed with a plurality of first through holes 120, each of which extends through the two electrode surfaces 121. The second electrode layer 12 may have a length ranging from 1 mm to 10 mm, a width ranging from 1 mm to 10 mm, and a thickness ranging from 350 nm to 1000 nm. Each of the first through holes 120 may independently have a diameter ranging from 50 nm to 200 nm.

The first and second electrode layers 11, 12 are independently made of a material that may include, a metal, a metal compound, and an organic conductive material, but is not limited thereto. Examples of the metal may include, but are not limited to, aluminum, gold, silver, calcium, nickel, and chromium. Examples of the metal compound may include, but are not limited to, indium tin oxide, zinc oxide, molybdenum oxide, and lithium fluoride. An example of the organic conductive material may include, but is not limited to, poly(3,4-ethylenedioxythiophene) polystyrene sulfonate (PEDOT:PSS). In the first embodiment, the first electrode layer 11 is made of indium tin oxide, and the second electrode layer 12 is made of aluminum. In a variation of the first embodiment, the second electrode layer 12 includes a plurality of interconnected nanowires.

The gas sensing layer 21 is stacked between and electrically interconnects the first electrode layer 11 and the second electrode layer 12 that are spaced apart from each other in a first direction (X) in this embodiment. The gas sensing layer 21 is adapted for contacting gas through the first through holes 120 of the second electrode layer 12. The gas sensing layer 21 may have a length ranging from 1 mm to 10 mm, a width ranging from 1 mm to 10 mm, and a thickness that is less than 5 µm. The gas sensing layer 21 is present in a form other than a hydrogel.

The gas sensing layer 21 is made of a hygroscopic electrically insulating material. Examples of the hygroscopic electrically insulating material suitable for use in this disclosure may include, but are not limited to, a hydroxyl-containing material, an amine-containing material, a carboxyl-containing material, and combinations thereof.

Examples of the hydroxyl-containing material may include, but are not limited to, polyethylene glycol (abbreviated as PEG), ethylene glycol monomethyl ether (abbreviated as EGME), poly(4-vinylphenol) (abbreviated as PVP), poly (vinyl alcohol) (abbreviated as PVA), and combinations thereof. In an exemplary embodiment, the gas sensing layer 21 is made of polyethylene glycol, such that the gas sensor has excellent air stability.

Examples of the carboxyl-containing material may include, but are not limited to, poly(acrylic acid) (abbreviated as PAA), poly(methacrylic acid) (abbreviated as PMAA), and a combination thereof. In another exemplary embodiment, the gas sensing layer 21 is made of poly (acrylic acid), such that the gas sensor has excellent air stability.

Examples of the amine-containing material may include, but are not limited to, polyethylenimine (abbreviated as PEI), diisopropanolamine (abbreviated as DIPA), a melamine resin, and combinations thereof.

In use, upon contact with the gas sensing layer 21, the gas to be detected reacts with the gas sensing layer 21 made of the hygroscopic electrically insulating material that absorbs water vapor in a humid environment, such that the gas is dissociated to generate conductive substances, such as ammonium ions ($NH_4^+$) generated by reacting ammonia ($NH_3$) with water, hydrosulfide ions ($HS^{-1}$) generated by reacting hydrogen sulfide ($H_2S$) with water, bicarbonate ions ($HCO_3^-$) or carbonate ions ($CO_3^{2-}$) generated by reacting carbon monoxide (CO) with water, etc. Therefore, the detection sensitivity of the gas sensor can be improved.

Figure 2:
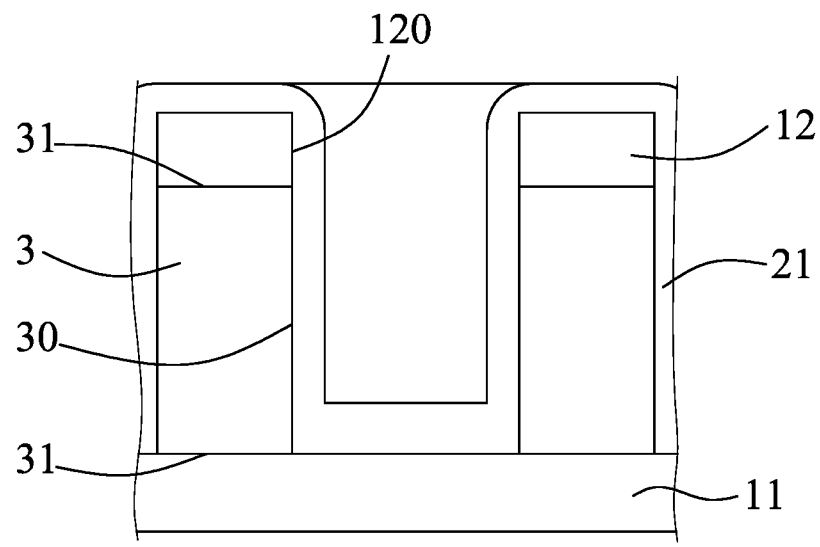
FIG. 2 is a fragmentary schematic sectional view illustrating a second embodiment of the gas sensor according to the present disclosure.
Figure 3:
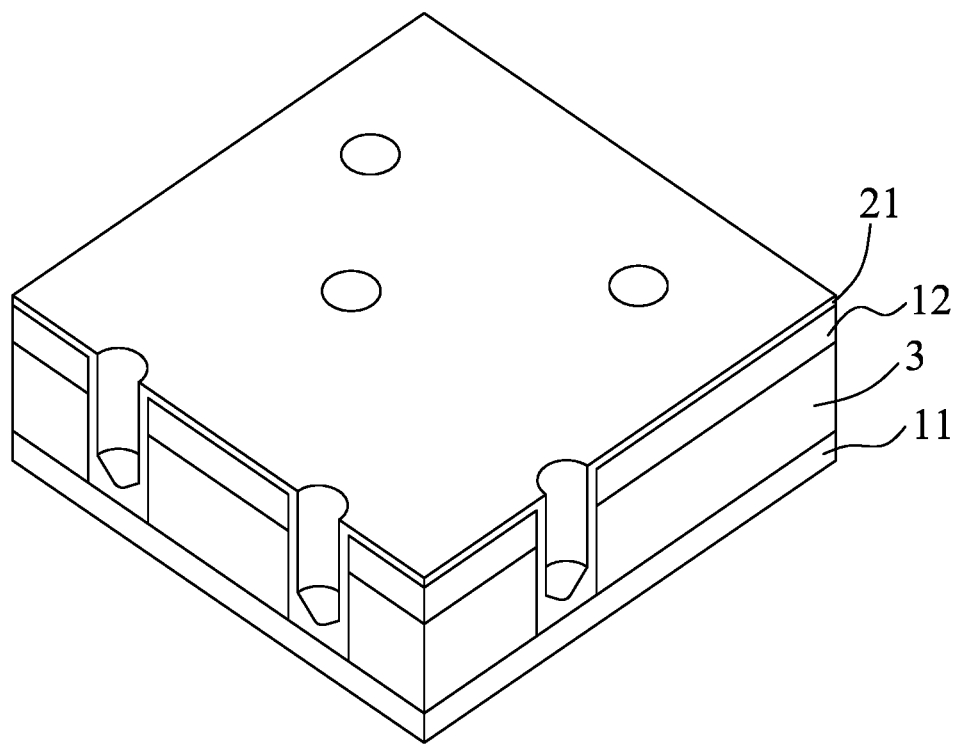
FIG. 3 is a partial perspective view of FIG. 2.

Referring to FIGS. 2 and 3, a second embodiment of the gas sensor according to the present disclosure is shown to be generally similar to the first embodiment, except for the following differences.

To be specific, in the second embodiment, the gas sensor further includes a dielectric layer 3 that is stacked between the first electrode layer 11 and the second electrode layer 12. The dielectric layer 3 has two dielectric surfaces 31 opposite to each other and is formed with a plurality of third through holes 30. Each of the third through holes 30 extends through the two dielectric surfaces 31 and is in spatial communication with a respective one of the first through holes 120. The dielectric layer 3 may have a length ranging from 1 mm to 10 mm, a width ranging from 1 mm to 10 mm, and a thickness ranging from 200 nm to 400 nm. Each of the third through holes 30 may independently have a diameter ranging from 50 nm to 200 nm. The dielectric layer 3 may be made of a material that may include, polyvinylphenol (abbreviated as PVP), polymethylmethacrylate (abbreviated as PMMA), a photoresist material, and polyvinyl alcohol (abbreviated as PVA), but is not limited thereto. An example of the photoresist material may include, but is not limited to, SU-8 negative photoresist (commercially available from M & R Nano Technology Co.; Ltd., Taiwan). In this embodiment, the dielectric layer 3 is made of polyvinylphenol having a weight average molecular weight of 25000 Da (Manufacturer: Sigma Aldrich; Model No.: AL-436224).

In addition, the gas sensing layer 21 is disposed on the second electrode layer 12, and extends into the first and third through holes 120, 30 to be electrically connected to the first electrode layer 11. That is, the first and third through holes 120, 30 are partially filled with the gas sensing layer 21.

Figure 4:
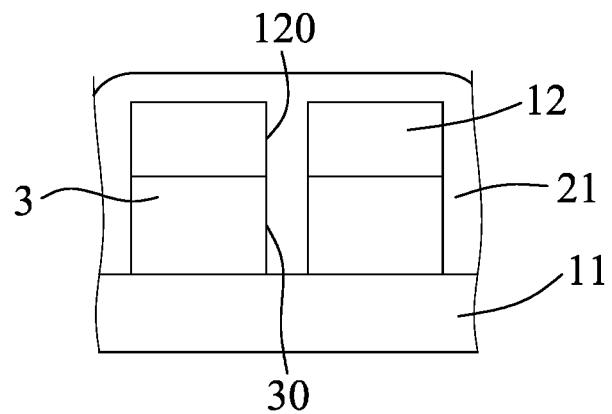
FIG. 4 is a fragmentary schematic sectional view illustrating a third embodiment of the gas sensor according to the present disclosure.

Referring to FIG. 4, a third embodiment of the gas sensor according to the present disclosure is shown to be generally similar to the second embodiment, except that, in the third embodiment, the gas sensing layer 21 is disposed on and covers the second electrode layer 12, and fills the first and third through holes 120, 30.

Figure 5:
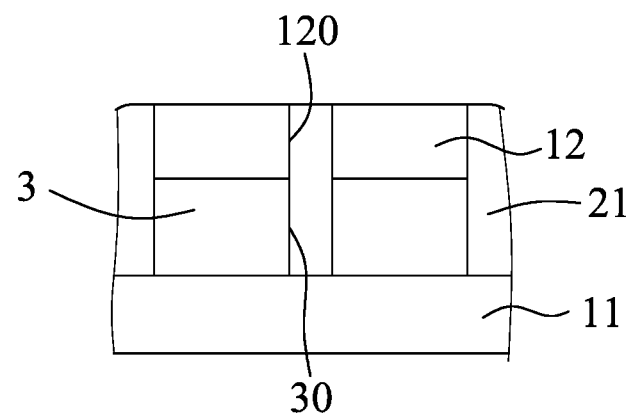
FIG. 5 is a fragmentary schematic sectional view illustrating a fourth embodiment of the gas sensor according to the present disclosure.

Referring to FIG. 5, a fourth embodiment of the gas sensor according to the present disclosure is shown to be generally similar to the third embodiment, except that, in the fourth embodiment, the gas sensing layer 21 does not cover the second electrode layer 12 and is flushed flush with the second electrode layer 12.

Figure 6:
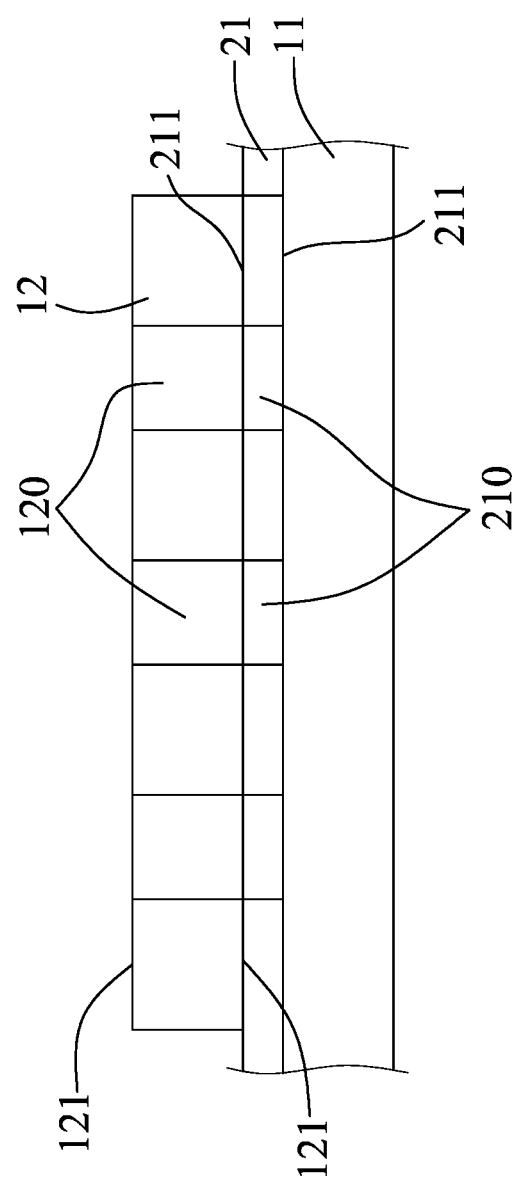
FIG. 6 is a fragmentary schematic sectional view illustrating a fifth embodiment of the gas sensor according to the present disclosure.

Referring to FIG. 6, a fifth embodiment of the gas sensor according to the present disclosure is shown to be generally similar to the first embodiment, except that, in the fifth embodiment, the gas sensing layer 21 has two sensing surfaces 211 opposite to each other and is formed with a plurality of second through holes 210, each of which extends through the two sensing surfaces 211 and is in spatial communication with a respective one of the first through holes 120.

Figure 7:
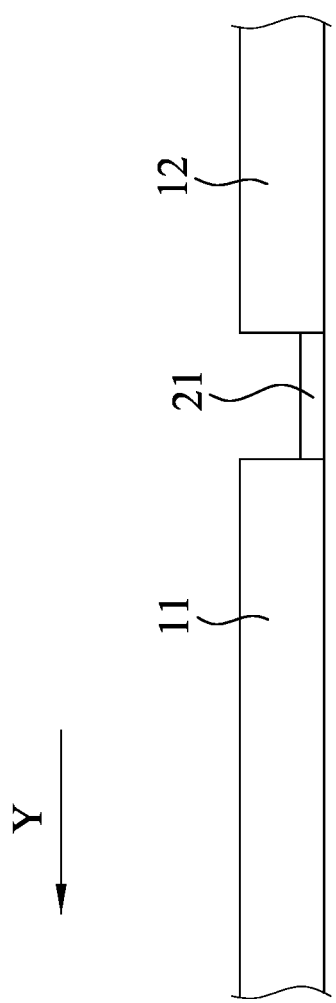
FIG. 7 is a fragmentary schematic sectional view illustrating a sixth embodiment of the gas sensor according to the present disclosure.

Referring to FIG. 7, a sixth embodiment of the gas sensor according to the present disclosure is shown to be generally similar to the first embodiment, except for the following differences.

To be specific, in the sixth embodiment, the second electrode layer 12 is not formed with the first through holes 120, and the first electrode layer 11 and the second electrode layer 12 are spaced apart from each other in a second direction (Y), i.e., a direction transverse to the first direction (X). The gas sensing layer 21 is disposed between the first electrode layer 11 and the second electrode layer 12. In addition, the first electrode layer 11 and the second electrode layer 12 are spaced apart by a distance in submicron range, so as to improve the detection sensitivity of the gas sensor. That is, the gas sensing layer 21 has a width that is equal to the distance between the first and second electrode layers 11, 12.

The disclosure will be further described by way of the following examples. However, it should be understood that the following examples are intended solely for the purpose of illustration and should not be construed as limiting the disclosure in practice.

EXAMPLES

Experimental Materials:
1. Hydroxyl-Containing Material

The hydroxyl-containing material used in the following examples includes polyethylene glycol (Manufacturer: Sigma-Aldrich; MDL No.: MFCD00081839; weight average molecular weight: 1500 Da), poly(4-vinylphenol) (Manufacturer: Sigma-Aldrich; MDL No.:

MFCD00147948; weight average molecular weight: 25,000 Da), ethylene glycol monomethyl ether (Manufacturer: Sigma-Aldrich; MDL No.: MFCD00002867), and poly(vinyl alcohol) (Manufacturer: Sigma-Aldrich; MDL No.: MFCD00081922; weight average molecular weight: 10000 Da), which are respectively abbreviated as "PEG", "PVP", "EGME", and "PVA" in Table 1 below.

2. Carboxyl-Containing Material

The carboxyl-containing material used in the following examples includes poly(acrylic acid) (Manufacturer: Sigma-Aldrich; MDL No.: MFCD00084394; weight average molecular weight: 1800 Da), which is abbreviated as "PAA" in Table 1 below.

Examples 1 to 21 (EX1 to EX21)

The gas sensors of EX1 to EX5 and EX8 to EX21 have the same structural configuration as shown in FIGS. 2 and 3 (i.e., the second embodiment as described above), while the gas sensors of EX6 and EX7 have the same structural configuration as shown in FIG. 6 (i.e., the fifth embodiment as described above). The hygroscopic electrically insulating material (abbreviated as HEIM) for making the gas sensing layer 21 of the respective example is shown in Table 1.

In testing, each of the gas sensors of EX1 to EX21 was placed in a chamber under a relative humidity (RH) controlled at a predetermined level (see Table 1). Next, the first electrode layer 11 and the second electrode layer 12 of the gas sensor were electrically connected to an external electrical device (Manufacturer: Agilent Technologies, Inc.; Model No.: U2722A) that includes a voltage supply for providing an applied voltage and a current detector for detecting current change. Thereafter, a gas to be tested (i.e., $NH_3$, CO, NO, $H_2S$ or acetone) in a specific concentration shown in Table 1 was introduced into the chamber to contact with the gas sensor of the respective one of EX1 to EX21 for a predetermined time period of 30 seconds under the applied voltage of 5 V, and the current was traced using the current detector. The current change percentage for each of the gas sensors of EX1 to EX21 before and after introduction of the gas to be tested in the specified concentration was calculated using the following formula:

$$A=[(B-C)/C]\times 100\%$$

where A=current change percentage
B=current value at the end of the predetermined contact time period
C=current value prior to introduction of the gas to be tested The thus calculated current change percentage for each of the gas sensors of EX1 to EX21 is shown in Table 1 below.

TABLE 1

| | | | Current change percentage (%) Concentration of gas introduced into the chamber | | | | | | | | | | | | | |
|---|---|---|---|---|---|---|---|---|---|---|---|---|---|---|---|---|
| | | | Part per billion (ppb) | | | | | | | | | | Parts per million (ppm) | | | |
| | HEIM | Tested gas | RH (%) | 5 | 10 | 15 | 20 | 30 | 50 | 100 | 200 | 300 | 400 | 500 | 1 | 2 | 5 | 10 |
| EX1 | PEG | $NH_3$ | 16 | 3.5 | 10 | 27.8 | 45 | 86 | 166 | 366 | — | — | — | — | — | — | — | — |
| EX2 | PEG | $NH_3$ | 23.8 | 5 | 22 | — | 45 | — | 120 | 200 | 319 | — | — | — | — | — | — | — |
| EX3 | PEG | $NH_3$ | 36 | 5.6 | — | 18.8 | — | 42 | 98 | 129 | — | — | — | — | — | — | — | — |
| EX4 | PEG | $NH_3$ | 62 | — | — | — | x | x | 8 | 19 | 67 | — | — | — | — | — | — | — |
| EX5 | PEG | CO | 36 | — | — | — | — | — | — | x | — | — | — | — | — | — | — | — |
| EX6 | PVP | $NH_3$ | 63.3 | — | — | — | — | — | — | — | — | 239 | — | 316 | 454 | 553 | 679 | 743 |
| EX7 | PVP | Acetone | 63.5 | — | — | — | — | — | — | — | — | — | — | 1 | 2 | 8 | 13 | 22 |
| EX8 | EGME | $NH_3$ | 15.6 | — | — | — | — | — | — | — | — | — | — | 10 | 15 | 23 | 35.5 | 51 |
| EX9 | EGME | $NH_3$ | 35.8 | — | — | — | — | — | — | — | — | — | — | 7.5 | 13 | 19 | 30 | 39 |
| EX10 | EGME | $NH_3$ | 55.1 | — | — | — | — | — | — | — | — | — | — | 6 | 10 | 14 | 21 | 31 |
| EX11 | EGME | Acetone | 15.5 | — | — | — | — | — | — | — | — | — | — | — | — | 2.7 | 6.4 | 7.6 |
| EX12 | EGME | Acetone | 35.9 | — | — | — | — | — | — | — | — | — | — | — | — | 1.3 | 3.8 | 6 |
| EX13 | EGME | Acetone | 54.7 | — | — | — | — | — | — | — | — | — | — | — | — | 0.8 | 1.9 | 6 |
| EX14 | EGME | NO | 15.3 | — | — | — | — | — | — | — | — | — | — | 22 | 36 | 70 | 121 | 282 |
| EX15 | EGME | NO | 35.8 | — | — | — | — | — | — | — | — | — | — | 26 | 49 | 85 | 146 | 300 |
| EX16 | EGME | NO | 55.7 | — | — | — | — | — | — | — | — | — | — | 23 | 48 | 87 | 163 | 349 |
| EX17 | PAA | $NH_3$ | 33 | — | — | — | — | — | — | 2.2 | — | 17 | 33 | 46.2 | — | — | — | — |
| EX18 | PAA | $NH_3$ | 36 | — | — | — | — | — | — | 5.1 | 13 | — | — | 70 | — | — | — | — |
| EX19 | PAA | CO | 36 | — | — | — | — | — | — | x | 3 | — | — | — | — | — | — | — |
| EX20 | PAA | $H_2S$ | 36 | — | — | — | — | — | — | x | 2.6 | — | — | — | — | — | — | — |
| EX21 | PVA | $NH_3$ | 53 | — | — | — | — | — | — | 4.2 | — | 9.8 | — | 15 | 48 | — | — | — |

"—": not determined; "x": not detected

It can be seen from Table 1 that the gas sensors of EX1 to EX21 have a gas detection capacity of about 10 ppm and lower, even down to ppb levels, indicating that the gas sensor according to this disclosure exhibits high sensitivity for detecting a gas of interest.

In summary, through the gas sensing layer 21 that is made of a hygroscopic electrically insulating material, the gas sensor of this disclosure is capable of sensing various types of gases, such as $NH_3$, CO, NO, $H_2S$, acetone, etc. in a humid environment.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the present disclosure has been described in connection with what is considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A gas sensor comprising:
 a first electrode layer;
 a second electrode layer spaced apart from said first electrode layer; and
 a gas sensing layer interconnecting said first electrode layer and said second electrode layer, the gas sensing layer made of a hygroscopic electrically insulating material and configured to transition between an insulative state before a gas to be detected contacts therewith and a conductive state when the gas to be detected contacts therewith in a humid environment, wherein the gas is dissociated to generate conductive substances upon contact with water.

2. The gas sensor as claimed in claim 1, wherein said hygroscopic electrically insulating material is selected from the group consisting of a hydroxyl-containing material, an amine-containing material, a carboxyl-containing material, and combinations thereof.

3. The gas sensor as claimed in claim 2, wherein said hydroxyl-containing material of said gas sensing layer is selected from the group consisting of polyethylene glycol, ethylene glycol monomethyl ether, poly(4-vinylphenol), poly(vinyl alcohol), and combinations thereof.

4. The gas sensor as claimed in claim 2, wherein said amine-containing material of said gas sensing layer is selected from the group consisting of polyethylenimine, diisopropanolamine, a melamine resin, and combinations thereof.

5. The gas sensor as claimed in claim 2, wherein said carboxyl-containing material of said gas sensing layer is selected from the group consisting of poly(acrylic acid), poly(methacrylic acid), and a combination thereof.

6. The gas sensor as claimed in claim 2, wherein said first electrode layer and said second electrode layer are spaced apart from each other in a second direction, said gas sensing layer being disposed between said first electrode layer and said second electrode layer.

7. The gas sensor as claimed in claim 1, wherein said second electrode layer has two electrode surfaces opposite to each other, and is formed with a plurality of first through holes each extending through said two electrode surfaces to permit contact of a gas with said gas sensing layer.

8. The gas sensor as claimed in claim 7, wherein said gas sensing layer is stacked between said first electrode layer and said second electrode layer that are spaced apart from each other in a first direction.

9. The gas sensor as claimed in claim 8, wherein said gas sensing layer has two sensing surfaces opposite to each other and is formed with a plurality of second through holes, each of said second through holes extending through said two sensing surfaces and being in spatial communication with a respective one of said first through holes.

10. The gas sensor as claimed in claim 7, further comprising a dielectric layer that is stacked between said first electrode layer and said second electrode layer, that has two dielectric surfaces opposite to each other, and that is formed with a plurality of third through holes, each of said third through holes extending through said two dielectric surfaces and being in spatial communication with a respective one of said first through holes.

11. The gas sensor as claimed in claim 10, wherein said gas sensing layer extends into said first and third through holes to be connected to said first electrode layer.

12. The gas sensor as claimed in claim 10, wherein said gas sensing layer covers said second electrode layer and fills said first and third through holes.

13. The gas sensor as claimed in claim 10, wherein said gas sensing layer fills said first and third through holes, and is flush with said second electrode layer.

14. A gas sensor, comprising:
 a first electrode layer;
 a second electrode layer spaced apart from said first electrode layer; and
 a gas sensing layer interconnecting said first electrode layer and said second electrode layer, the gas sensing layer made of a hygroscopic electrically insulating material,
 wherein said second electrode layer has two electrode surfaces opposite to each other, and is formed with a plurality of first through holes each extending through said two electrode surfaces to permit contact of a gas with said gas sensing layer,
 wherein said gas sensing layer is stacked between said first electrode layer and said second electrode layer that are spaced apart from each other in a first direction, and
 wherein said gas sensing layer has two sensing surfaces opposite to each other and is formed with a plurality of second through holes, each of said second through holes extending through said two sensing surfaces and being in spatial communication with a respective one of said first through holes.

* * * * *